United States Patent [19]

Werner et al.

[11] Patent Number: 4,661,621

[45] Date of Patent: Apr. 28, 1987

[54] PROCESS FOR THE PREPARATION OF PIVALOYLACETIC ACID ESTERS

[75] Inventors: Friedrich Werner, Cologne; Heinz U. Blank, Odenthal, both of Fed. Rep. of Germany

[73] Assignee: Bayer Aktiengesellschaft, Leverkusen, Fed. Rep. of Germany

[21] Appl. No.: 686,188

[22] Filed: Dec. 26, 1984

Related U.S. Application Data

[63] Continuation of Ser. No. 200,695, Oct. 27, 1980, abandoned.

[30] Foreign Application Priority Data

Nov. 12, 1979 [DE] Fed. Rep. of Germany ....... 2945604

[51] Int. Cl.$^4$ .................. C07C 67/333; C07C 69/716
[52] U.S. Cl. ..................................... 560/174; 564/136
[58] Field of Search ........................................ 560/174

[56] References Cited

U.S. PATENT DOCUMENTS 2,527,306  10/1950  Halverstadt ........................ 560/174

OTHER PUBLICATIONS

House, Modern Synthetic Reactions, 2nd ed., 1972, pp. 747–750.

Snyder et al., Organic Synthesis, 1943, Col. vol. 2, pp. 531–534.

Primary Examiner—Vivian Garner
Attorney, Agent, or Firm—Sprung, Horn, Kramer & Woods

[57] ABSTRACT

An improved process for the preparation of pivaloylacetic acid esters by decarbonylation of pivaloylpyruvic acid esters at elevated temperatures is described. The process is carried out in the presence of 0.01 to 5 percent by weight of a metal of sub-groups one to eight of the periodic system, which metal is in metallic and/or oxidic form. Initially, 30 percent of the pivaloylpyruvic acid ester to be converted is heated in the presence of the metal, and after conversion of the same there is added additional pivaloylpyruvic acid ester according to the rate at which the pivaloylpyruvic acid ester is converted.

6 Claims, No Drawings

PROCESS FOR THE PREPARATION OF PIVALOYLACETIC ACID ESTERS

This is a continuation of application Ser. No. 200,695, filed Oct. 27, 1980, now abandoned.

The invention relates to a process for the preparation of pivoloylacetic acid esters by decarbonylation of pivaloylpyruvic acid esters.

It is known to obtain pivaloylacetic acid methyl ester in a yield of 80% of the theoretical yield by heating a mixture of pivaloylpyruvic acid methyl ester and about 11% by weight, relative to the pivaloylpyruvic acid ester, of powdered glass to about 175° C. for 5½ hours (U.S. Pat. No. 2,527,306). The danger of this process is that when the reaction starts suddenly, large amounts of carbon monoxide are formed in a short time. The sudden rise in pressure which thereby occurs can lead to the destruction of the apparatus. Moreover, the carbon monoxide liberated is dangerous, because of its toxicity.

A process has now been found for the preparation of pivoloylacetic acid esters by decarbonylation of pivaloylpyruvic acid esters at elevated temperature, which is characterized in that at most 30% of the pivaloylpyruvic acid ester to be converted is first heated in the presence of 0.01 to 5% by weight, relative to the toal amount if pivaloylpyruvic acid ester to be converted, of a metal of sub-groups one to eight of the periodic system of the elements (Mendeleev) in metallic and/or oxidic form, and after the decarbonylation reaction has started, the remaining amount of the pivaloylpyruvic acid ester is added according to the rate at which it is converted.

Pivaloylpyruvic acid esters which are employed in the process according to the invention are those of the formula $$(CH_3)_3C—CO—CH_2—CO—COOR \quad (I)$$

in which R represents alkyl or cycloalkyl.

Alkyl radicals which may be mentioned are straight-chain or branched aliphatic hydrocarbon radicals with 1 to 10, preferably 1 to b 4 and particularly preferably 1 to 2, carbon atoms, such as methyl, ethyl, propyl, isopropyl, butyl, isobutyl, hexyl, octyl and decyl.

Examples of cycloalkyl radicals which may be mentioned are saturated carbocyclic hydrocarbon radicals which have 3 to 8, preferably 5 to 6, carbon atoms and are optionally substituted by methyl or ethyl groups, for example cyclopropyl, cyclobutyl, cyclopentyl, methylcyclopentyl, ethyl-cyclopentyl, cyclohexyl, methylcyclohexyl, ethyl-cyclohexyl, cycloheptyl and cyclooctyl.

The process according to the invention is carried out at elevated temperature. A temperature of 130° to 230° C., preferably 170° to 200° C., may be mentioned as an example.

In the process according to the invention, the decarbonylation of the pivaloylpyruvic acid ester is carried out in the presence of 0.01 to 5% by weight, preferably 0.2 to 1% by weight, of a metal of sub-groups one to eight of the periodic system of the elements (Mendeleev) in metallic and/or oxidic form. Examples of such metals which may be mentioned are: copper, silver, zinc, cadmium, scandium, yttrium, titanium, zirconium, vanadium, niobium, chromium, molybdenum, tungsten, manganese, iron, cobalt, nickel, ruthenium, rhodium and palladium.

The metals can be employed in their metallic and/or oxidic form as such or on suitable supports. Mixtures of the metals in their metallic and/or oxidic form in any desired composition can likewise be used. It is also possible to employ salts or other compounds of the metals mentioned, if these salts or other compounds are converted into the metallic or oxidic form under the conditions of the process according to the invention.

The process according to the invention is preferably carried out in the presence of a metal from the iron group, that is to say iron, cobalt or nickel, in its metallic and/or oxidic form.

Iron and iron-containing metals, and oxides thereof, or mixtures of iron or iron-containing metals and their oxides are very particularly preferred for the process according to the invention. Examples which may be mentioned here are ground iron which is optionally contaminated by other metals and optionally partially oxidised, such as iron scrap.

In the process according to the invention, at most 30% of the pivaloylpyruvic acid ester to be converted is first brought to the desired reaction temperature in the presence of one of the metals mentioned, in metallic and/or oxidic form. An amount of, for example, 1 to 30%, preferably 2 to 20%, may be mentioned, as at most 30% of the pivaloylpyruvic acid ester to be converted. When the reaction has started, this being characterized by the evolution of carbon monoxide, the remaining amount of the pivaloylpyruvic acid ester is added, in portions or continuously, and according to the rate at which it is consumed, to the reaction in progress.

This addition of the remaining amount of the pivaloylpyruvic acid ester may be carried out at a rate of from 0.2 to 4 mols pivaloylpyruvic acid ester for each mol of the same which is decarbonylated. The preferred rate is from 0.5 to 1.5 mols added ester; the especially preferred rate is from 0.8 to 1.2 mols added ester.

Pivaloylacetic acid esters of the formula $$(CH_3)_3C—CO—CH_2—COOR \quad (II)$$

in which R represents alkyl or cycloalkyl,
can be prepared with the aid of the process according to the invention. In this formula, alkyl and cycloalkyl have the same scope of meaning as in the case of formula (I).

The reaction of the process according to the invention may be represented by the following equation, by reference to the preparation of pivaloylacetic acid methyl ester by decarbonylation of pivaloylpyruvic acid methyl ester:

$$(CH_3)_3C—CO—CH_2—CO—COOCH_3 \rightarrow (CH_3)_3C—CO—CH_2—COOCH_3 + CO$$

The process according to the invention is in general carried out without using a solvent. However, it is also possible to use a solvent which is stable under the reaction conditions.

The pivaloylacetic acid esters prepared by the process according to the invention can be reacted further with equimolar amounts of aniline or substituted anilines by heating for 1 hour in boiling xylene to give the optionally substituted α-pivaloylacetanilides, which are couplers for yellow dyestuffs in color photography (U.S. Pat. No. 3,265,506).

It is surprising that high yields of pivaloylacetic acid esters which are greater than the yields of the state of the art are achieved in the presence of the metals mentioned, in metallic and/or oxidic form, without relatively substantial decomposition of the substances participating in the reaction.

By using the said metals, in metallic and/or oxidic form, as auxiliaries, the process according to the invention requires less auxiliaries than processes according to the state of the art. Furthermore, always only a small, purity of 99.2% (according to analysis by gas chromatography). $n_D^{25} = 1.4315$.

EXAMPLE 3-9

The following results are achieved using the catalysts and temperatures given in the Table in a procedure analogous to that in Example 2:

| Example | Catalyst | Temperature °C. | Amount of ester initially introduced g | Amount of ester added dropwise g | Total reaction time hours | yield % of theory | Selectivity |
|---------|-----------|-----|----|-----|-------|-------|-------|
| 3 | Fe turnings | 190 | 40 | 160 | 3½ | 90.4 | 90.4 |
| 4 | Cu powder | 195 | 40 | 160 | 13½ | 75.5 | 75.5 |
| 5 | Ni—on-SiO$_2$ | 182 | 40 | 160 | 5½ | 86.1 | 86.1 |
| 6 | Mn powder | 190 | 40 | 160 | 8 | 79.5 | 79.5 |
| 7 | Cr powder | 200 | 40 | 160 | 8 | 61.5* | 87.7 |
| 8 | Mo powder | 190 | 40 | 160 | 5½ | 86.9 | 86.9 |
| 9 | Co powder | 190 | 40 | 160 | 8 | 84.0 | 84.0 |

*Selectivity: 87.7% controllable amount of pivaloylpyruvic acid ester is decarbonylated in the process according to the invention. Nevertheless, high space/time yields which, in the preferred form of the process according to the invention, are better than those of the state of the art are achieved.

EXAMPLE 1

40 g of pivaloylpyruvic acid ethyl ester and 4 g of iron turnings are heated to 190° C. After 0.5 hour, 3 l of CO have been formed. A further 360 g of ester are added dropwise in the course of 4½ hours, whereupon a further 46 l of gas are formed. The mixture is allowed to cool and 295 g (85.8% of the theoretical yield) of pivaloylacetic acid ethyl ester are distilled out of the reaction mixture, at boiling point$_{18}$:78° C., with a purity of 99% (according to analysis by gas chromatography). $n_D^{25}$:1.4310.

EXAMPLE 2

20 g of pivaloylpyruvic acid methyl ester and 2 g of iron turnings are heated to 180° C., whilst stirring. After about 40 minutes, 1.5 l of CO have been formed. 180 g of ester are added dropwise in the course of 3½ hours. A total of 25.2 l of CO are formed. Distillation at boiling point$_{20}$:82° C. gives 157.3 g of pivaloylacetic acid methyl ester (92.1% of the theoretical yield) with a

What is claimed is:

1. In a process for the preparation of a pivaloylacetic acid ester by decarbonylation of a pivaloylpyruvic acid ester at an elevated temperature, the improvement which comprises subjecting pivaloylpyruvic acid ester to decarbonylation by heating the same in the presence of 0.01 to 5 percent by weight, relative to the total amount of the pivaloylpyruvic acid ester to be converted, of a metal in metallic and/or oxidic form, said metal being selected from the group consisting of copper, manganese, chromium and molybdenum, such that at most 30 percent of the total amount of the pivaloylpyruvic acid ester to be converted is heated and thereafter following the commencement of the reaction, adding the remaining amount of the pivaloylpyruvic acid ester to be converted according to the rate at which it is converted.

2. A process according to claim 1, wherein the metal is in an amount of 0.2 to 1% by weight.

3. A process according to claim 1 wherein said metal is copper.

4. A process according to claim 1 wherein said metal is manganese.

5. A process according to claim 1 wherein said metal is chromium.

6. A process according to claim 1 wherein said metal is molybdenum.

* * * * *